United States Patent [19]

Peglion et al.

[11] Patent Number: 5,194,437
[45] Date of Patent: Mar. 16, 1993

[54] 1,4-DISUBSTITUTED PIPERAZINES

[75] Inventors: Jean-Louis Peglion, Le Vesinet; Mark Millan, Paris; Jean-Michel Rivet, Nanterre, all of France

[73] Assignee: Adir et Compagnie, Courbevoie, France

[21] Appl. No.: 807,106

[22] Filed: Dec. 13, 1991

[30] Foreign Application Priority Data

Dec. 14, 1990 [FR] France .................................. 90 15631

[51] Int. Cl.$^5$ .................. A61K 31/495; C07D 407/04; C07D 321/08; C07D 319/16
[52] U.S. Cl. ..................................... 514/254; 544/377
[58] Field of Search ......................... 544/377; 514/254

[56] References Cited

U.S. PATENT DOCUMENTS

| 4,684,651 | 8/1987 | Kikumoto et al. | 544/377 |
| 4,782,061 | 11/1988 | Kruse et al. | 544/377 |
| 5,002,948 | 3/1991 | Perregaard et al. | 544/366 |

FOREIGN PATENT DOCUMENTS

| 90203 | 10/1983 | European Pat. Off. | 544/377 |
| 2494584 | 5/1982 | France | 544/377 |
| 7080379 | 5/1982 | Japan | 544/377 |

OTHER PUBLICATIONS

Perregaard et al., CA 114-17582m (1990) Computer Search printout is provided.

Primary Examiner—Cecilia Tsang
Attorney, Agent, or Firm—Gordon W. Hueschen

[57] ABSTRACT

The compounds are 1,4-disubstituted piperazines useful for the treatment of disorders of central nervous system and neuroendocrine disorders.

A compound disclosed is (R,S)-4-(benzodioxan-5-yl)-1-[(benzocyclobutan-1-yl)methyl]piperazine.

14 Claims, No Drawings

1,4-DISUBSTITUTED PIPERAZINES

The present invention relates to 1,4-disubstituted piperazines of formula I:

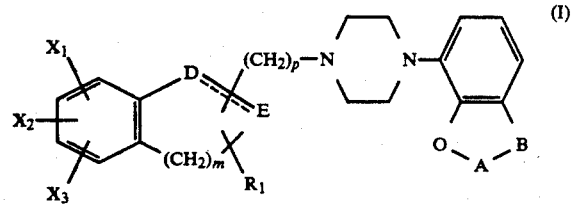

in which:

$X_1$, $X_2$ and $X_3$,
which are the same or different, each represent: a hydrogen or halogen atom, a straight-chained or branched-chained alkyl radical containing from 1 to 5 carbon atoms, a hydroxy radical, a straight-chained or branched-chained alkoxy or alkylthio radical each containing from 1 to 5 carbon atoms, a trifluoromethyl radical, a nitro radical, an amino radical or an acetamido radical, or two of them in adjacent positions together form a methylenedioxy radical or an ethylenedioxy radical;

$R_1$ represents a hydrogen atom or a straight-chained or branched-chained alkyl radical containing from 1 to 5 carbon atoms;

-D═E- represents: —(CH$_2$)$_n$—(CH$_2$)— or —CH═CH—;

each of m and n represents 0, 1, 2 or 3, provided that m+n≧1;

p represents 0 or an integer from 1 to 6; and

-A-B- represents a radical of the formula: —(CH$_2$)$_2$—O—; —(CH$_2$)$_3$—O—; —CH═CH—; —CH$_2$—CH$_2$—; or

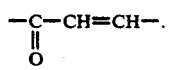

Some compounds of formula I contain an asymmetric carbon atom and can therefore be separated into optical isomers, which are also included in the present invention.

The prior art in this field is illustrated especially by the European patent applications published under Nos. 38,280; 185,429; 189,612; 307,061; and 376,607.

None of those applications either describes or suggests the compounds to which the present invention relates, which compounds have a pharmacological activity of the 5-HT$_{1A}$ antagonist type, which is not the case with the compounds of the prior art mentioned above.

The present invention relates also to a process for the preparation of the compounds of formula I, characterised in that:

an N-monosubstituted piperazine of formula II:

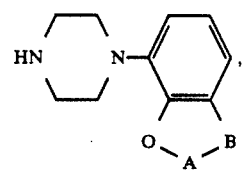

in which the group -A-B- has the meaning defined above, is condensed:

with a compound of the general formula III

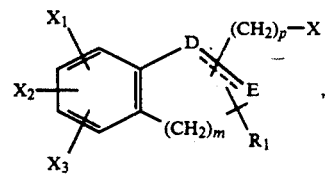

in which:
$X_1$, $X_2$, $X_3$, $R_1$, -D═E-, m and p have the meanings defined above, and X represents a halogen atom, or a mesyloxy or tosyloxy radical.

It is especially appropriate to carry out the condensation in a suitable solvent, such as, for example, methyl ethyl ketone, methyl isobutyl ketone, toluene or dimethylformamide, in the presence of an acceptor for the acid formed during the reaction, at a temperature of from 20° to 150° C. There may be used as the acceptor, for example, an alkali metal carbonate, such as sodium carbonate, or a tertiary amine, such as triethylamine.

Moreover, the compounds of formula I in which p is other than 0, that is to say the compounds that correspond more precisely to formula I':

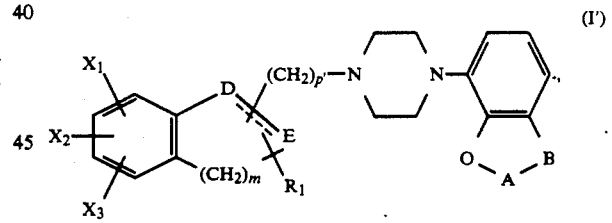

in which:
$X_1$, $X_2$, $X_3$, $R_1$, -D═E-, m and -A-B- have the meanings defined above, and p' represents an integer from 1 to 6, have also been prepared according to a variant of the above process, which variant is characterised in that:

the N-monosubstituted piperazine of formula II defined above is condensed with:

a compound of formula IV

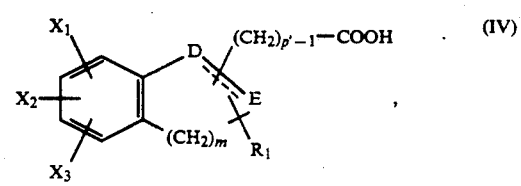

in which:

$X_1$, $X_2$, $X_3$, $R_1$, -D=E-, m and p', have the meanings defined above; and the resulting amide of formula V:

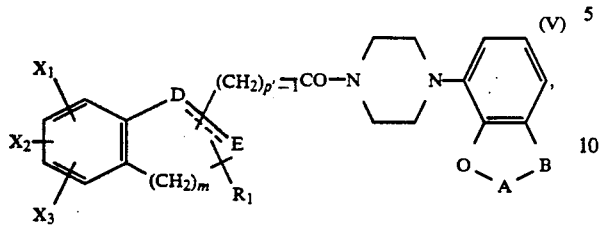

in which:

$X_1$, $X_2$, $X_3$, $R_1$, -D=E-, m, p' and -A-B- have the meanings defined above, is reduced.

It is especially appropriate to carry out the condensation of the compounds II and IV in a suitable solvent, such as, for example, methylene chloride, in the presence of carbonyldiimidazole.

The amide V is advantageously reduced by means of a double hydride of lithium and aluminium in a suitable solvent, such as, for example, ether or tetrahydrofuran.

The latter process for the preparation of the compounds I' is likewise included in the present invention.

Moreover, the amides of formula V are new intermediates which, as such, form part of the present invention.

The starting materials of formulae II, III and IV are either known products or products prepared from known compounds according to known processes, as specified in the Examples below.

The compounds of formula I yield salts with physiologically tolerable acids. Those salts are likewise included in the present invention.

The compounds of the present invention have valuable pharmacological and therapeutic properties. In fact, pharmacological tests have shown that the compounds of the invention behave, in vitro and in vito, like very powerful and very selective ligands of $5-HT_{1A}$ serotonin receptors, with an antagonist activity towards that neurotransmitter at the level of the central nervous system, as is demonstrated by the pharmacological study exemplified below.

This activity enables the compounds of the present invention to be used in the treatment of disorders of the central nervous system, especially of anxiety, pain, depression, psychosis, schizophrenia, migraine, perceptual disorders, stress and anorexia, and of neuroendocrine disorders, such as diabetes.

The present invention also relates to pharmaceutical compositions that contain as active ingredient a compound of formula I or a physiologically tolerable salt thereof, in admixture or in association with a suitable pharmaceutical excipient, such as, for example, glucose, lactose, talc, ethylcellulose, magnesium stearate or cocoa butter.

The pharmaceutical compositions so obtained are generally in dosage unit form and may contain from 0.1 to 100 mg of active ingredient. They may be in the form of, for example, tablets, dragées, soft gelatin capsules, suppositories or injectable or drinkable solutions, and may be administered orally, rectally or parenterally, as appropriate, in a dose of from 0.1 to 100 mg of active ingredient from 1 to 3 times per day.

The following Examples illustrate the present invention, melting points being determined using a Kofler hot-plate (K), optionally under a microscope (M.K).

EXAMPLE 1

(R,S)-4-(benzodioxan-5-yl)-1-[(benzocyclobutan-1-yl)methyl]-piperazine:

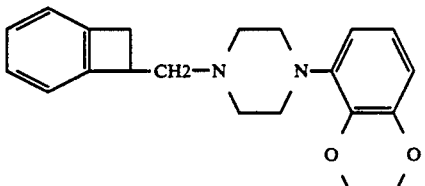

4 g ($16.4 \times 10^{-3}$ mol) of (benzocyclobutan-1-yl)-methyl iodide, 3.61 g ($16.4 \times 10^{-3}$ mol) of N-(benzodioxan-5-yl)piperazine, 6.95 g ($65.5 \times 10^{-3}$ mol) of $Na_2CO_3$, and 100 ml of methyl isobutyl ketone are mixed, and the whole is heated under reflux for 24 hours, with stirring. The reaction mixture is concentrated using a rotary evaporator, and the concentrate is taken up in $CH_2Cl_2$. After washing with water, the organic phase is extracted with a normal hydrochloric acid solution. The aqueous phase is rendered alkaline and then extracted with $CH_2Cl_2$. Drying and concentration yield 4.4 g of an oil, which is crystallised in ether. The resulting solid is recrystallised in 15 ml of isopropyl ether, yielding 1.6 g of (R,S)-4-(benzodioxan-5-yl)-1-[(benzocyclobutan-1-yl)methyl]-piperazine, m.p. (M.K): 91°–95° C., yield: 29%, which was subjected to thin layer chromatography (solvents: methylene chloride-methanol, 90–10).

NMR (solvent: $CDCl_3$):

4H (m) 7.3–7.0 ppm; 1H (t) 6.8 ppm; 2H (m) 6.6 ppm; 4H (m) 4.3 ppm; 1H (m) 3.7 ppm; 1H (dd) 3.4 ppm; 4H (m) 3.10 ppm; 2H (m) 2.85 ppm; 4H (m) 2.7 ppm; 1H (dd) 2.65 ppm.

The N-(benzodioxan-5-yl)-piperazine used as starting material was prepared according to the method described in J. Med. Chem. (1988) 31, 1934, from 1-nitro-2,3-dihydroxybenzene, which is itself described in J.A.C.S. (1953), 3277.

The compounds of Examples 2 to 5 were prepared in the same manner.

EXAMPLES 2 TO 5

2) (R,S)-4-(benzodioxan-5-yl)-1-[2-(benzocyclobutan-1-yl)-ethyl]-piperazine and its dihydrochloride, m.p. (M.K): 215°–226° C. (with sublimation from 192° C.) (yield: 56%), from 2-(benzocyclobutan-1-yl)-ethyl bromide (prepared from the corresponding alcohol as described in the French patent application filed on Nov. 7, 1989 under no. 89.14571) and N-(benzodioxan-5-yl)-piperazine, in the presence of $Na_2CO_3$, by heating under reflux in methyl isobutyl ketone for 8 hours.

3) (R,S)-4-[benzo(1,5)dioxepin-6-yl]-1-[2-(benzocyclobutan-1-yl)-ethyl]-piperazine and its hydrochloride, m.p. (M.K): 170°–210° C. (with sublimation), yield: 51%, from 2-(benzocyclobutan-1-yl)-ethyl bromide and N-(benzo(1,5)dioxepin-6-yl)-piperazine, which is itself described in J. Med. Chem. (1988) 31, 1934.

4) (R,S)-4-(benzofuran-7-yl)-1-[2-(benzocyclobutan-1-yl)ethyl]-piperazine and its hydrochloride, m.p.

(M.K): 192°-195° C. (isopropanol) (yield: 47%), from 2-(benzocyclobutan-1-yl)-ethyl bromide and N-(benzofuran-7-yl)piperazine, which was itself prepared, in a yield of 49%, according to the method described in J. Med. Chem. (1988) 31, 1934, from di-(2-chloroethyl)-amine hydrochloride and 7-aminobenzofuran hydrochloride, which was itself obtained by reduction of 7-nitrobenzofuran.

The latter was prepared from 2-ethoxycarbonyl-7-nitrobenzofuran, which was itself obtained from 2-hydroxy-3-nitrobenzaldehyde, which was itself formed by nitration of 2-hydroxybenzaldehyde.

5) (R,S)-4-(benzodioxan-5-yl)-1-[2-(3-chlorobenzocyclobutan-1-yl)-ethyl]-piperazine and its dihydrochloride, m.p. (M.K): 207°-211° C. (methyl cyanide), from 2-(3-chlorobenzocyclobutan-1-yl)-ethyl bromide (oil, b.p./0.1 mmHg 80° C.) and N-(benzodioxan-5-yl)-piperazine (yield: 54%). 2-(3-chlorobenzocyclobutan-1-yl)-ethyl bromide was prepared from (3-chlorobenzocyclobutan-1-yl)-carboxylic acid which, when treated with LiAlH₄ and then with tosyl chloride, yields (3-chlorobenzocyclobutan-1-yl)-methyl tosylate, m.p. (K): 60°-62° C. (yield: 84%), which is treated with sodium cyanide in dimethyl sulphoxide and then with potassium hydroxide in an aqueous ethanol solution and is finally reduced to form (3-chlorobenzocyclobutan-1-yl)-methylcarboxylic acid, m.p. (K): 94°-96° C., which is then treated with LiAlH4 and then with PBr₃ in benzene to give the desired bromide in a yield of 41%.

EXAMPLE 6

(R,S)-4-[benzo(1,5)dioxepin-6-yl]-1-[(benzocyclobutan-1-yl)-methyl]-piperazine:

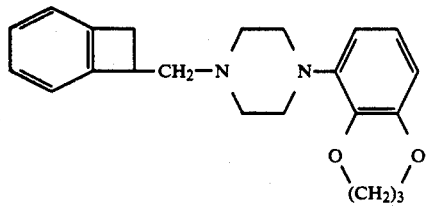

4 g (13.8×10⁻³ mol) of (benzocyclobutan-1-yl)-methyl tosylate, 3.3 g (13.8×10⁻³ mol) of N-benzo(1,5-)dioxepin-6-yl)-piperazine, 3.9 ml (27.6×10⁻¹ mol) of triethylamine and 50 ml of toluene are mixed, and the whole is heated under reflux for 24 hours. The reaction mixture is concentrated using a rotary evaporator and the concentrate is taken up in H₂O and CH₂Cl₂. The organic phase is extracted with a normal hydrochloric acid solution. The aqueous phase is rendered alkaline and then extracted with CH₂Cl₂. Drying yields 2.1 g of a solid, which is dissolved in 20 ml of ethanol. 1.7 ml of 3.5N ethyl chloride are added to that ethanolic solution, and the whole is left in a refrigerator for 48 hours. The resulting precipitate is filtered and dried, yielding 2 g of (R,S)-4-[benzo(1,5)dioxepin-6-yl]-1-[(benzocyclobutan-1-yl)-methyl]-piperazine, m.p. (M.K): 248°-252)20 C. (with sublimation from 190° C.), yield: 37%, which was subjected to thin layer chromatography (solvents: methylene chloride-methanol, 95-5).

The compounds of Examples 7 to 10 were prepared in the same manner.

EXAMPLES 7 TO 10

7) 4-(benzodioxan-5-yl)-1-(indan-2-yl)-piperazine, m.p. (M.K): 168°-171° C., from indan-2-yl tosylate [cf. Bull. Soc. Chem. (1962), p. 51] and N-(benzodioxan-5-yl)piperazine (yield: 11%).

8) (R,S)-4-(benzodioxan-5-yl)-1-[4-(benzocyclobutan-1-yl)-butyl]-piperazine and its fumarate, m.p. (M.K): 180°-183° C. (ethanol), from 4-(benzocyclobutan-1-yl)-butyl mesylate (oil) and N-(benzodioxan-5-yl)-piperazine dihydrochloride (yield: 44%).

4-(benzocyclobutan-1-yl)-butyl mesylate was prepared, in a yield of 96%, by treating 4-(benzocyclobutan-1-yl)butanol (oil) with CH₃SO₂Cl in the presence of triethylamine in methylene chloride.

9) 4-[benzo(1,5)dioxepin-6-yl]-1-(indan-2-yl)-piperazine, m.p. (M.K): 138°-140° C., from indan-2-yl tosylate and N-[benzo(1,5)dioxepin-6-yl]-piperazine [cf. J. Med. Chem. (1988), p. 1935] (yield: 20%).

10) 4-(coumarin-8-yl)-1-(indan-2-yl)-piperazine, m.p. (M.K): 162°-163° C. (acetonitrile), from indan-2-yl tosylate and N-(coumarin-8-yl)-piperazine, m.p. (K): >260° C. (sublimation). Yield: 28%.

N-(coumarin-8-yl)-piperazine was prepared by reacting 8-aminocoumarin with an excess of bis(2-chloroethyl)amine hydrochloride in the presence of potassium carbonate and then of potassium iodide, the reaction being carried out under reflux in chlorobenzene.

8-aminocoumarin was obtained from the corresponding nitrated derivative according to Archiv. der Pharmazie, (1963), 296 (6), 365-369;

which nitrated derivative was itself prepared from o-hydroxybenzaldehyde according to Fort. Hase Papers (1975), 6 (2), 109-118.

EXAMPLE 11

(R,S)-4-(benzodioxan-5-yl)-1-[(3-chlorobenzocyclobutan-1-yl)-methyl]-piperazine

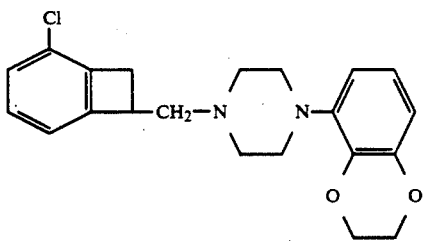

a) First step 0.1 mol of N,N-carbonyldiimidazole is added in a single batch, under a nitrogen atmosphere, to 0.1 mol of (3-chlorobenzocyclobutan-1-yl)-carboxylic acid in 100 ml of methylene chloride, and the two are left in contact for 2 hours. Then 0.1 mol of N-(benzodioxan-5-yl)-piperazine dissolved in 50 ml of methylene chloride is rapidly added dropwise. The two are left in contact for one night, with stirring. Evaporation is then carried out, the residue is taken up in ether, the organic phase is extracted with a normal hydrochloric acid solution, and then the aqueous phases are rendered alkaline at reduced temperature.

Evaporation and chromatography of the residual oil (solvents: methylene chloride-ethyl acetate, 90-10) yield (R,S)-4-(benzodioxan-5-yl)-1-[(3-chlorobenzocyclobutan-1-yl)-carbonyl]-piperazine, m.p. (K): 182°-184° C., yield: 40%.

NMR (solvent: CDCl₃):
3H, 7.25 and 7.05 ppm (m); 1H, 6.8 ppm (t); 2H, 6.7 to 6.5 ppm (d); 1H, 4.5 ppm (m); 4H, 4.25 to 4 ppm (m); 4H, 3.85 ppm; 2H, 3.65 and 3.45 ppm (dd); 4H, 3.05 ppm (t+t).

(3-chlorobenzocyclobutan-1-yl)-carboxylic acid used as starting material was prepared, as described in the European patent application filed by the applicant under no. 90403145.7, from 3-chloro-1-cyanobenzocyclobutane, which is itself described in European Patent 119,107.

b) Second step 0.1 mol of (R,S)-4-(benzodioxan-5-yl)-1-[(3-chlorobenzocyclobutan-1-yl)-carbonyl]-piperazine, prepared as described above, in 100 ml of tetrahydrofuran is added dropwise, under a nitrogen atmosphere, to a suspension of 0.1 mol of lithium aluminium hydride in 50 ml of tetrahydrofuran. The mixture is left at room temperature for one night, with stirring. Decomposition is carried out, in an ice-bath, by means of $H_2O$: 2.6 ml, 20% NaOH: 2.1 ml and $H_2O$: 9.5 ml.

The precipitate is filtered and the filtrate is evaporated. The residual oil is chromatographed on fine silica using the system $CH_2Cl_2$-$CH_3OH$ (95-5) as eluant, yielding (R,S)-4-(benzodioxan-5-yl)-1-[(3-chlorobenzocyclobutan-1-yl)-methyl]-piperazine in a yield of 72%.

NMR (solvent: $CDCl_3$):

3H, 7.2 to 6.95 ppm (m); 1H, 6.8 ppm (t); 2H, 6.55 ppm (m); 4H, 4.25 ppm (m); 1H, 3.7 ppm (m); 2H, 3.5 to 3.25 ppm (m); 4H, 3.1 ppm (m); 6H, 3 to 2.7 ppm (m).

A solution of 0.05 mol of the base so obtained in 20 ml of ether is stirred for 15 minutes with 10 ml of normal hydrochloric acid. The mixture is then filtered and rinsed with ether, and (R,S)-4-(benzodioxan-5-yl)-1-[(3-chlorobenzocyclobutan-1-yl)-methyl]-piperazine hydrochloride, m.p. (K):>260° C. with sublimation, is recrystallised from water. (Yield: 30%).

EXAMPLES 12 TO 29

The compounds of the following Examples were prepared following the procedure described in Example 11:

12) (R,S)-4-(benzodioxan-5-yl)-1-[(3-fluorobenzocyclobutan-1-yl)-methyl]-piperazine and its hydrochloride, m.p. (K): 254°-256° C. with sublimation, by reduction of (R,S)-4-(benzodioxan-5-yl)-1-[(3-fluorobenzocyclobutan-1-yl)-carbonyl]-piperazine (yield: 48%), which was itself prepared in a yield of 40% from (3-fluorobenzocyclobutan-1-yl)-carboxylic acid [which was itself prepared according to the method described in Tetrahedron (1974), 30, 1053, from 3-fluorobenzaldehyde]and N-(benzodioxan-5-yl)-piperazine.

13) (R,S)-4-(benzodioxan-5-yl)-1-[3-(benzocyclobutan-1-yl)-propyl]-piperazine and its hydrochloride, m.p. (K): 206°-208° C., by reduction of 4-(benzodioxan-5yl)-1-[3-(benzocyclobutan-1-yl)-propionyl ]-piperazine (yield: 65%), which was itself prepared in a yield of 37% from 3-(benzocyclobutan-1-yl)-propionic acid (described in the patent application filed by the applicant under no. 90403145.7) and N-(benzodioxan-5-yl)-piperazine.

14) 4-(benzodioxan-5-yl)-1-[(indan-2-yl)-methyl]-piperazine and its hydrochloride, m.p. (K): 232°-234° C., by reduction of 4-(benzodioxan-5-yl)-1-[(indan-2-yl)carbonyl-piperazine, m.p. (K): 160°-162° C. (yield: 43%), which was itself prepared in a yield of 37% from (indan-2-yl)-carboxylic acid [described in J.A.C.S. (1975), 97, vol. 2, 347-353] and N-(benzodioxan-5-yl)-piperazine.

15) (R,S)-4-(benzodioxan-5-yl)-1-[(indan-1-yl)-methyl]-piperazine, m.p. (M.K): 87°-90° C., by reduction of 4-(benzodioxan-5-yl)-1-[(indan-1-yl)-carbonyl]-piperazine (yield: 70%), which was itself prepared in a yield of 41% from (indan-1-yl)-carboxylic acid [described in Synthesis (1987), 845] and N-(benzodioxan-5-yl)piperazine.

16) (R,S)-4-(benzodioxan-5-yl)-1-[2-(5-methoxybenzocyclobutan-1-yl)-ethyl]-piperazine (oily product) and its hydrochloride, m.p. (K): 192°-194° C., by reduction of 4-(benzodioxan-5-yl)-1-[2-(5-methoxybenzocyclobutan-1-yl)-actyl]-piperazine (oily product) (yield: 62%), which was itself prepared in a yield of 72% from 2-(5-methoxybenzocyclobutan-1-yl)-acetic acid and N-(benzodioxan-5-yl)-piperazine.

2-(5-methoxybenzocyclobutan-1-yl)-acetic acid was prepared according to the method described in J.A.C.S. (1975), 347, in a yield of 54%, from the corresponding nitrile, which is obtained, in a yield of 97%, from the corresponding tosylate, which was itself prepared, in a yield of 76%, from the corresponding alcohol and paratoluene sulphonyl chloride, in a pyridine medium.

17) (R,S)-4-(benzodioxan-5-yl)-1-[2-(4,5-dimethoxybenzocyclobutan-1-yl)-ethyl]-piperazine (oil) and its hydrochloride, (K): 232°-234°C., by reduction of 4-(benzodioxan-5-yl)-1-[2-(4, 5-dimethoxybenzocyclobutan-1-yl)-acetyl]-piperazine (oil) (yield: 59%), which was itself prepared in a yield of 51.5% from 2-(4,5-dimethoxybenzocyclobutan-1-yl)-acetic acid and N-(benzodioxan-5-yl)piperazine.

2-(4,5-dimethoxybenzocyclobutan-1-yl)-acetic acid, m.p. (K): 136°-139°C., was itself obtained, in a yield of 96%, according to the method described in J.A.C.S. (1975), 347, from the corresponding nitrile, m.p. (K): 110°-112°C.

18) 4-(benzodioxan-5-yl)-1-[2-(ind-1-en-1-yl)-ethyl]-piperazine and its hydrochloride, m.p. (K): 254°-256° C., by reduction of 4-(benzodioxan-5-yl)-1-[2-(ind-1-en-1-yl)-acetyl]-piperazine (yield: 30%), which was itself prepared in a yield of 66% from 2-(ind-1-en-1-yl)acetic acid [m.p. (K): 92°-94° C.]and N-(benzodioxan-5-yl)piperazine.

2-(ind-1-en-1-yl)-acetic acid was prepared according to the method of H. Ahmed and N. Campbell J.C.S. (1960), 4115-4120, in a yield of 90%, from ethyl 2-(indan-1-ylidene)-acetate, which was itself prepared in a yield of 48% from indan-1-one and $(C_6H_5)_3P{=}CH{-}COOC_2H_5$ in toluene.

19) (R,S)-4-(benzodioxan-5-yl)-1-[2-(5,6-dimethoxyindan-1-yl)-ethyl]-piperazine and its hydrochloride, m.p. (K): 225°-226° C. (methanol), by reduction of 4-(benzodioxan-5-yl)-1-[2-(5, 6-dimethoxyindian-1-yl)-acetyl]-piperazine (yield: 25%), which was itself prepared in a yield of 98% from 2-(5,6-dimethoxyindan-1-yl)-acetic acid, m.p. (K) 151°-153° C., and N-(benzodioxan-5-yl)-piperazine.

2-(5,6-dimethoxyindan-1-yl)-acetic acid was prepared in a yield of 79% from the corresponding ethyl ester (oil), which was obtained in a yield of 97% from ethyl 2-(5,6-dimethoxyindan-1-ylidene)-acetate, which was itself prepared in a yield of 25% from 5,6-dimethoxyindan-1-one and $(C_6H_5)_3P{=}CH{-}COOC_2H_5$ in toluene.

20) 4-(benzodioxan-5-yl)-1-[2-(indan-2-yl)-ethyl]-piperazine, m.p (M.K): 121°-123° C., by reduction of 4-(benzodioxan-5-yl)-1-[2-(indan-2-yl)-acetyl ]-piperazine (oil) (yield: 64%), which was itself prepared in a yield of 90% from 2-(indan-2-yl)-acetic acid, m.p. (M.K): 91°-93° C., and N-(benzodioxan-5-yl)-piperazine.

2-(indan-2-yl)-acetic acid was prepared from the corresponding ethyl ester (oil), which was obtained in a yield of 98% by hydrogenation of ethyl 2-(indan-2-ylidene)acetate (oil), which was itself prepared in a yield of 74% from indan-2-one and $(C_6H_5)_3P=CH-COOC_2H_5$ in toluene.

21) (R,S)-4-(benzofuran-7-yl)-1-[3-(benzocyclobutan-1-yl)-propyl]-piperazine and its fumarate, m.p. (M.K): 197°-200°C. (methanol), by reduction of 4-(benzofuran-7-yl)-1-[3-(benzocyclobutan-1-yl)-propionyl]-piperazine (oil) (yield: 47%), which was itself prepared in a yield of 57% from 3-(benzocyclobutan-1-yl)-propionic acid and N-(benzofuran-7-yl)-piperazine, prepared according to J. Med. Chem. (1988), 31, 1934–1940.

22) (R,S)-4-(benzodioxan-5-yl)-1-[2-(indan-1-yl)-ethyl]-piperazine and its hydrochloride, m.p. (K): 220°-222° C., by reduction of 4-(benzodioxan-5-yl)-1-[2-(indan-1-yl)acetyl]-piperazine (yield: 44%), which was itself prepared in a yield of 75% from 2-(indan-1-yl)-acetic acid and N-(benzodioxan-5-yl)-piperazine.

23) (R,S)-4-(benzodioxan-5-yl)-1-[3-(indan-1-yl)-propyl]piperazine and its dihydrochloride, m.p. (K): 175°-185° C., by reduction of 4-(benzodioxan-5-yl)-1-[3-(indan-1-yl)propionyl]-piperazine (oil) (yield: 71.5%), which was itself prepared in a yield of 85% from 3-(indan-1-yl)propionic acid (oil) and N-(benzodioxan-5-yl)-piperazine.

3-(indan-1-yl)-propionic acid was prepared as follows: 27 g of 1-indanecarboxylic acid methyl ester [obtained according to the method of F. M. Nongrun and B. Myrboh, Synthesis (1987) 9, 845–846] in 200 ml of sodium hydroxide and 200 ml of ethanol are stirred at room temperature for one night. Acidification with concentrated hydrochloric acid yields 8 g of 1-indanecarboxylic acid, m.p. (K): 65° C. (yield: 30%).

8 g of the acid so obtained in 200 ml of tetrahydrofuran are added to a suspension of 1.55 g of lithium aluminium hydride in 40 ml of tetrahydrofuran and stirred at room temperature for one night. After hydrolysis by means of 1.07 ml of water then 0.86 ml of 20% sodium hydroxide, and finally 4 ml of water, and evaporation of the solvent, the residue is distilled using a Kügelrohr. 4.3 g of 1-indanemethanol are obtained (oil; b.p./0.05 mmHg 70°-75° C.) (yield: 58%).

10 g of that alcohol and 19 g of p-toluene sulphonyl chloride are stirred in 80 ml of pyridine for 18 hours. After evaporation of the solvent, the medium is washed with water and extracted with $CH_2Cl_2$. 14 g of 1-indanemethanol tosylate are obtained in the form of an oil, in a yield of 70%. 5 g of the tosylate so obtained dissolved in 5 ml of ethanol are added to a mixture of 3.2 g of diethyl malonate, which has itself been added dropwise to a solution of sodium ethoxide obtained from 0.46 g of sodium in 10 ml of ethanol. The reaction medium is then brought to reflux and kept under reflux for 18 hours. After dilution with hydrochloric acid, the product is extracted with ethyl acetate and purified on a silica column using $CH_2Cl_2$/cyclohexane (40/60) as eluant. 3-(indan-1-yl)-2-ethoxycarbonylpropionic acid ethyl ester is thus obtained in a yield of 56%.

2.3 g of that ester are refluxed in 5 ml of water and 2.5 g of potassium hydroxide for 2 hours. Acidification with HCl yields 1.8 g of 3-(indan-1-yl)-2-carboxypropionic acid, m.p. (K): 150°-152° C. (yield: 96%).

1.8 g of the diacid so obtained are refluxed in N,N-dimethylacetamide for 2 ½ hours. Dilution with water and extraction with ether yield 1.3 g of 3-(indan-1-yl)propionic acid in the form of an oil, in a yield of 89%.

24) (R,S)-4-[benzo(1,5)dioxepin-6-yl]-1-[3-(benzocyclobutan-1-yl)-propyl]-piperazine and its hydrochloride, m.p. (M.K): 262°-265°-C., by reduction of 4-[benzo(1,5)dioxepin-6-yl]-1-[3-(benzocyclobutan-1-yl)-propionyl]-piperazine (oil) (yield: 37%), which was itself prepared in a yield of 30% from 3-(benzocyclobutan-1-yl)propionic acid and N-[benzo(1,5)dioxepin-6-yl]piperazine.

25) 4-(benzodioxan-5-yl)-1-[3-(indan-2-yl)-propyl]-piperazine and its hydrochloride, m.p. (K): 210° C., by reduction of 4-(benzodioxan-5-yl)-1-[3-(indan-2-yl)propionyl]-piperazine (yield: 50%), which was itself prepared in a yield of 86% from 3-(indan-2-yl)-propionic acid, m.p. (K): 75°-78° C., and N-(benzodioxan-5-yl)piperazine.

3-(indan-2-yl)-propionic acid was prepared in a yield of 68% from 3-(indan-2-yl)-2-carboxypropionic acid, which was prepared in a yield of 44% from the corresponding diethyl ester, which was itself obtained in a yield of 69% from (indan-2-yl)-ethyl mesylate and di(ethoxycarbonyl)methane.

26) (R,S)-4-(benzodioxan-5-yl)-1-[3-(3-chlorobenzocyclobutan-1-yl)-propyl]-piperazine and its dihydrochloride, m.p. (M.K): 223° 226° C., by reduction of 4-(benzodioxan-5-yl)-1-[3-( 3-chlorobenzocyclobutan-1-yl)-propionyl]-piperazine, m.p. (K): 135°-140° C. (yield: 84%), which was itself prepared in a yield of 74% from 3-(3-chlorobenzocyclobutan-1-yl)-propionic acid (oil) and N-(benzodioxan-5-yl)-piperazine.

3-(3-chlorobenzocyclobutan-1-yl)-propionic acid was prepared in a yield of 61% from 3-(3-chlorobenzocyclobutan-1-yl)-2-carboxypropionic acid, m.p. (K): 190°-192° C., which was prepared in a yield of 100% from the corresponding diethyl ester, which was itself obtained in a yield of 30% from (3-chlorobenzocyclobutan-1-yl)-methyl tosylate and di(ethoxycarbonyl)methane.

27) (R,S)-4-(benzodioxan-5-yl)-1-[2-(1,2,3,4-tetrahydronaphthalen-1-yl)-ethyl]-piperazine and its hydrochloride, instantaneous m.p.: 250°-252° C. (acetonitrile), by reduction of 4-(benzodioxan-5-yl)-1-[2-(1,2,3,4-tetrahydronaphthalen-1-yl)-acetyl]-piperazine, which was itself prepared from (1,2,3,4-tetrahydronaphthalen-1-yl)acetic acid and N-(benzodioxan-5-yl)-piperazine.

(1,2,3,4-tetrahydronaphthalen-1-yl)-acetic acid was itself prepared from 1-ethoxycarbonylmethyl-1,2,3,4-tetrahydronaphthalene, which was obtained from 1-ethoxycarbonylmethyl-3,4-dihydronaphthalene [cf. J. Chem. Soc. (1960), 4115–4120], which was itself prepared from 1,2,3,4-tetrahydronaphthalen-1-one.

28) (R,S)-4-(benzodioxan-5-yl)-1-[2-(benzocycloheptan-1-yl)-ethyl]-piperazine and its dihydrochloride, m.p. (M.K): 179°-186° C., by reduction of 4-(benzodioxan-5-yl)-1[2-( benzocycloheptan-1-yl)-acetyl]-piperazine, which was itself prepared from (benzocycloheptan-1-yl)-acetic acid and N-(benzodioxan-5-yl)-piperazine.

(Benzocycloheptan-1-yl)-acetic acid was prepared from 1-ethoxycarbonylmethylbenzocycloheptane, which was itself prepared from benzocycloheptan-1-one.

29) 4-(benzodioxan-5-yl)-1-[2-(benzocyclohept-1-en-1-yl)ethyl]-piperazine and its hydrochloride, m.p. (M.K): 33°-236° C., by reduction of 4-[(benzodioxan-5-yl)-1-(benzocyclohept-1-en-1-yl)-acetyl]-piperazine, which was itself prepared from (benzocyclohept-1-en-1-yl)-acetic acid and N-(benzodioxan-5-yl)-piperazine.

(Benzocyclohept-1-en-1-yl)-acetic acid was prepared from 1-ethoxycarbonylmethylbenzocyclohept-1-ene, which was itself prepared from benzocycloheptan-1-one treated with

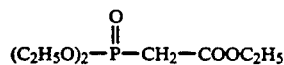

and NaH in tetrahydrofuran, followed by separation of the two exocyclic unsaturated cis- and trans-isomers also formed, the separation being carried out by flash chromatography on silica gel with toluene as eluant.

EXAMPLE 30

Pharmacological Study

The compounds of the present invention were studied in comparison with buspirone, a reference product which is known to be a ligand of serotonin $5\text{-}HT_{1A}$ receptors.

A) Method:

The tests were carried out on male Wistar rats weighing from 200 to 220 g which had free access to food and drinking water, in standard cages.

The animals are housed individually for the hypothermia, corticosterone secretion and flat body posture tests, and in groups of three for the tail flick test.

The laboratory temperature is kept at $21°\pm1°$ C., with $60\pm5\%$ humidity. The rats are subjected to a light/dark cycle of 12 hours/12 hours (the light cycle commencing at 7.30 a.m.).

1) In vitro study - Binding test

Hippocampus from the brains of decapitated rats was immediately frozen on dry ice and then stored at $-80°$ C. until preparation of membranes. The tissue was homogenised at $4°$ C. in the appropriate buffer using a Polytron (Brinkman Instruments - Lucerne - Switzerland) and centrifuged at 20,000 rpm.

Incubation was carried out at $25°$ C. for 30 minutes. Non-specific binding was defined by 10 $\mu M$ of 5-HT. The tests were terminated by rapid filtration by means of a Brandel harvester over glass-fibre filters pretreated with 0.1% polyethyleneimine.

For each cold ligand, a minimum of 3 values producing from 20 to 80% inhibition of binding of the hot ligand were taken into consideration. The inhibitory concentration 50 values ($IC_{50}$) were determined according to method 8 of Tallarida R. J. and Murray R. B., Manual of pharmacological calculations with computer programs, Springer Verlag, N.Y. (1987).

The pKi was calculated according to the formula $$pKi = -\log\left(\frac{IC_{50}}{1 + [L]/Kd}\right)$$

where [L] is the concentration of the hot ligand ([3]H-8-OH-DPAT, 0.4 nM) and Kd is the apparent dissociation constant determined from saturation experiments.

The test substances were dissolved in the incubation buffer.

2) In vivo study a/ General procedure for tests of agonist and antagonist activities on $5\text{-}HT_{1A}$ receptors.

The test compounds were administered subcutaneously (s.c.) 60 minutes before the start of the test, that is to say 30 minutes before the vehicle (agonist responses) or 8-OH-DPAT (antagonist responses).

In all the tests, the solvent is used in parallel as the control. The animals were allowed to rest in their cages during the time between the injections and evaluation.

For the agonist studies, the solvent was administered at a dose of 1 ml/kg s.c. 30 minutes before the start of the test. For the antagonist studies, doses of 8-OH-DPAT inducing sub-maximal responses were chosen, i.e. doses of 0.63, 0.16, 0.16 and 0.16 mg/kg s.c. for the tail flick test, the flat body posture test, the corticosterone secretion test and the hypothermia test, respectively.

b/ Flat body posture (FBP) and corticosterone secretion (CS).

The same animals were employed for the evaluation of the effect of the test compounds on the FBP and for the determination of the plasma levels of CS. All the tests were carried out in the morning between 10.30 and 12.30, i.e. when the cicardian levels of CS are at their lowest.

25 minutes after the treatment (i.e. 5 minutes before decapitation), the animals are observed in their cages and the presence or absence of FBP is noted.

The presence of FBP is defined by a characteristic posture of the animal. The animal is then in a position of ventral decubitus with the hind limbs clearly in extension. 5 minutes after observation of FBP, the animals are decapitated and the trunk blood is collected in chilled tubes containing 50 $\mu l$ of a 10% EDTA solution. After centrifugation at 4000 rpm, the plasma is removed and stored at $-30°$ C. until assay.

CS was determined using a radio-competitive assay for a CS-binding protein in plasma: transcortin. The latter is obtained from monkey serum. Separation of the CS-transcortin complexes from free CS was effected by means of a solution of dextran and active charcoal. The detection limit was 50 pg/tube. Intra- and inter-assay variations were 5 and 15%, respectively [cf. Rivet J. M. et al., Eur. J. Pharmacol., 183, 634–635 (1990)].

Since the base levels of CS in plasma are never zero, the following formula was used to calculate the percentage inhibition of plasmatic CS induced by 8-OH-DPAT:

$$\% \text{ inhibition} = 100 \times \frac{(\text{antagonist} + \text{agonist}) - \text{antagonist alone}}{(\text{solvent} + \text{agonist}) - \text{solvent alone}}$$

c/ Body temperature (BT)

The rats are immobilised and a lubricated digital thermometer (Thermistoprobe from Testotherm, Basle, Switzerland) is inserted into the rectum to a depth of 5 cm. 30 seconds after insertion, the temperature is read off a digital scale. The percentage inhibition is calculated with the aid of the formula mentioned above.

d/ Spontaneous tail flick test: (STF)

Tail flicks were determined in animals restrained in horizontal, opaque plastics cylinders, the animals' tails hanging freely over the edge of the laboratory bench. After a 5-minute adaptation period, the number of movements made in 5 minutes is recorded. One STF is defined as the raising of the tail to a level higher than the level of the body axis [Millan M. J. et al., J. Pharmacol. Exp. Ther., 256, 973–982 (1990)].

e/Analysis of in vivo results

In general, after variance analysis, the results are subjected to Dunnett's test. Results are regarded as significant if $p<0.05$.

For analysis of the dose-response curves for induction of STF, CS and hypothermia, the minimum effective dose (M.E.D.) in mg/kg was determined, i.e., the does that induces a response that is significantly different from that produced by the solvent.

For analysis of the dose-response curves for inhibition of STF, CS and hypothermia, the $ID_{50}$ values in mg/kg (dose that reduces the action of 8-OH-DPAT by 50%) were calculated together with the 95% confidence limits using a modification of the Finney method (1964).

For the dose-response for induction and inhibition of FBP, the effective doses 50 ($ED_{50}$) (doses at which 50% of the animals show a response) were calculated by the method of Litchfield and Wilcoxon.

f/Compounds studied

The doses of the test compounds are all expressed in terms of the base. Unless otherwise mentioned, all the compounds were dissolved in sterile water (to which a few drops of lactic acid are added, if necessary) and administered at a volume of 1 ml/kg s.c..

B) Results

The results are shown in Tables 1 and 2 below.

TABLE 1

| Binding of $5\text{-}HT_{1A}$ receptors | |
|---|---|
| COMPOUND | AFFINITY (pKi) |
| Reference product BUSPIRONE | 7.93 |
| Example 1 | 8.74 |
| Example 2 | 9.21 |
| Example 3 | 8.94 |
| Example 4 | 8.85 |
| Example 5 | 8.65 |
| Example 7 | 8.75 |
| Example 8 | 8.80 |

TABLE 1-continued

| Binding of $5\text{-}HT_{1A}$ receptors | |
|---|---|
| COMPOUND | AFFINITY (pKi) |
| Example 9 | 8.42 |
| Example 12 | 8.75 |
| Example 13 | 9.35 |
| Example 14 | 8.47 |
| Example 15 | 8.70 |
| Example 16 | 8.85 |
| Example 17 | 8.46 |
| Example 18 | 9.09 |
| Example 19 | 8.83 |
| Example 20 | 9.18 |
| Example 21 | 8.55 |
| Example 22 | 8.80 |
| Example 23 | 9.21 |
| Example 24 | 9.10 |

TABLE 2

IN VIVO AGONIST AND ANTAGONIST ACTIVITY OF $5\text{-}HT_{1A}$ RECEPTORS

| COMPOUND | SPONTANEOUS TAIL FLICKS | | FLAT BODY POSTURE $ED_{50}$ (95% C.L.) | | CORTI-COSTERONE SECRETION | | HYPOTHERMIA | |
|---|---|---|---|---|---|---|---|---|
|  | M.E.D. | $ID_{50}$ (95% C.L.) | AGONIST RESPONSE | ANTAGONISM OF 8-OH-DPAT | M.E.D. | $ID_{50}$ (95% C.L.) | M.E.D. | $ID_{50}$ (95% C.L.) |
| Reference product buspirone | >10.0 | 3.71 (1.40–9.84) | 7.4 (2.16–25.57) | >10.0 | >2.5 | >10.0 | 2.5 | — |
| Example 1 | >10.0 | 0.09 (0.02–0.32) | >10.0 | 0.71 (0.09–5.34) | >2.5 | <2.5 | 10.0 | 0.5 (0.2–1.24) |
| Example 2 | >10.0 | 0.085 (0.025–0.28) | >20.0 | 0.76 (0.23–2.58) | 10.0 | 0.66 (0.35–1.24) | 40.0 | 0.65 (0.36–1.14) |
| Example 3 | >10.0 | 0.32 (0.077–1.38) | >10.0 | 1.55 (0.76–3.17) | >10.0 | 2.15 (1.21–3.84) | >20.0 | 1.64 (0.83–3.25) |
| Example 7 | >10.0 | 0.74 (0.28–1.93) | >10.0 | 0.52 (0.18–1.48) | >10.0 | 2.5 | 20.0 | 1.60 (0.80–3.20) |
| Example 9 | >10.0 | 1.59 (0.77–3.3) | >2.5 | <2.5 | >2.5 | >2.5 | 5.0 | 4.36 (1.67–11.42) |
| Example 13 | >10.0 | 0.13 (0.054–0.32) | >10.0 | 0.57 (0.17–1.87) | 10.0 | 1.27 (0.59–2.73) | 10.0 | 0.21 (0.04–0.97) |
| Example 14 |  | 0.19 (0.05–0.74) | >2.5 | ≧2.5 | >2.5 | >2.5 | >10.0 | <2.5 |
| Example 15 |  | 0.085 (0.03–0.22) | >2.5 | ≧2.5 | >2.5 | >2.5 | 10.0 | 1.53 (0.57–4.06) |
| Example 20 |  | 0.18 (0.03–1.03) | >2.5 | <2.5 | >2.5 | <2.5 | 10.0 | 0.58 (0.22–1.49) |
| Example 22 | >10.0 | 0.74 (0.28–1.91) | >10.0 | 1.03 (0.52–2.03) | >10.0 | 1.92 (1.08–3.43) | >40.0 | 1.19 (0.59–2.42) |
| Example 23 |  | 0.56 (0.17–1.81) | 10.0 | 0.29 (0.06–1.55) | >2.5 | <2.5 | 5.0 | 0.40 (0.12–1.37) |

$ID_{50}$ = Inhibitory Dose 50; $ED_{50}$ = Effective Dose 50; CL = Confidence limits; MED = Minimum Effective Dose C) Conclusion The results recorded in Tables 1 and 2 show that the compounds of the present invention have an antagonist behaviour towards $5\text{-}HT_{1A}$ receptors, in contrast with buspirone which, although it also binds to the $5\text{-}HT_{1A}$ receptors, has an agonist behaviour.

Accordingly, the compounds of the present invention are valuable in the treatment of disorders of the central nervous system and of neuroendocrine disorders.

We claim:

1. A 1,4-disubstituted piperazine selected from those of formula I:

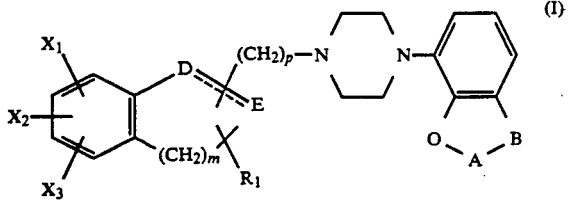

in which:

X₁, X₂ and X₃,
which are the same or different, each represent: hydrogen, halogen, straight-chained or branched-chained alkyl having 1 to 5 carbon atoms inclusive, hydroxy, straight-chained or branched-chained alkoxy or alkylthio each having 1 to 5 carbon atoms inclusive, trifluoromethyl, nitro, amino, or acetamido, or
two of them in adjacent positions together form methylenedioxy or ethylenedioxy;

$R_1$ represents hydrogen or straight-chained or branched-chained alkyl having 1 to 5 carbon atoms inclusive;

-D==E- represents: $-(CH_2)_n-(CH_2)-$ or $-CH=CH-$
wherein each of m and n represents 0, 1, 2 or 3, provided than m+n is at least 1;

p represents 0 or 1 to 6 inclusive; and

-A-B-represents: $-(CH_2)_2-O-$; $-(CH_2)_3-O-$; $-CH=CH-$; $-CH_2-CH_2-$; or

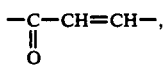

in racemic and optically active forms, and physiologically-tolerable acid addition salts thereof.

2. A compound of claim 1 which is selected from: (R,S)-4-(benzodioxan-5-yl)-1-[2-(benzocyclobutan-1-yl)-ethyl]-piperazine and its dihydrochloride.

3. A compound of claim 1 which is selected from: (R,S)-4-(benzodioxan-5-yl)-1-[2-(3-chlorobenzocyclobutan-1-yl)-ethyl]-piperazine and its dihydrochloride.

4. A compound of claim 1 which is: 4-(benzodioxan-5-yl)-1-(indan-2-yl)-piperazine.

5. A compound of claim 1 which is selected from: (R,S)-4-(benzodioxan-5-yl)-1-[4-(benzocyclobutan-1-yl)-butyl]-piperazine and its fumarate.

6. A compound of claim 1 which is: 4-[benzo(1,5)dioxepin-6-yl]-1-(indan-2-yl)-piperazine.

7. A compound of claim 1 which is selected from: (R,S)-4-(benzodioxan-5-yl)-1-[2-(ind-1-en-1-yl)-ethyl]-piperazine and its hydrochloride.

8. A compound of claim which is selected from: (R,S)-4-(benzodioxan-5-yl)-1-[2-(indan-1-yl)-ethyl]-piperazine and its hydrochloride.

9. A pharmaceutical composition comprising as active ingredient an effective 5-HT1A receptor antagonistic amount of a compound of claim 1 together with one or more suitable pharmaceutical excipients.

10. A method for treating a mammal afflicted with a condition requiring a 5-HT1A receptor antagonist for its treatment, comprising the step of administering to the said mammal an amount of a compound of claim 1 which is effective for alleviation of said condition.

11. As an intermediate, an amide of formula V:

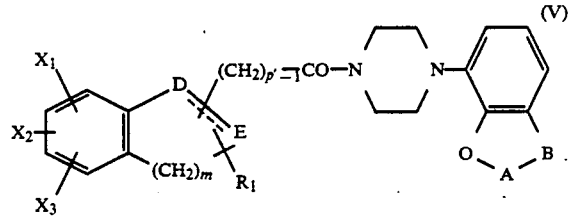

in which
X₁, X₂, X₃, R₁, -D==E-, m, and -A-B- have the meanings defined in claim 1, and
p' is 1 to 6 inclusive.

12. A compound of claim 1 which is selected from (R,S)-4-(benzodioxan-5-yl)-1-[2-(benzocyclobutan-1-yl)-ethyl]-piperazine and an acid addition salt thereof.

13. A compound of claim 1 which is selected from 4-(benzodioxan-5-yl)-1-(indan-2-yl)-piperazine and an acid addition salt thereof.

14. A compound of claim 1 which is selected from (R,S)-4-benzodioxan-5-yl)-1-[2-(indan-1-yl)-ethyl ]-piperazine and an acid addition salt thereof.

* * * * *

UNITED STATES PATENT AND TRADEMARK OFFICE
CERTIFICATE OF CORRECTION

PATENT NO. : 5,194,437

DATED : March 16, 1993

INVENTOR(S) : Jean Louis Peglion, Mark Millan, Jean-Michle Rivet

It is certified that error appears in the above-indentified patent and that said Letters Patent is hereby corrected as shown below:

Column 1, line 42; move the closing parenthesis and the subscript 2 ")$_2$" from the beginning of line 42 to the end of line 41 and insert before the hyphen.

Column 3, approximately line 42; "vito," should read --vivo--,.

Column 5, lines 45 and 46; move the closing parenthesis ")" from the beginning of line 46 to the end of line 45 and insert before the hyphen "-".

Column 5, line 46; "10$^{-1}$" should read -- 10$^{-3}$ --.

Column 5, line 59; "-252)20 C." should read -- -252° C. --.

Column 7, line 55; "5yl" should read -- 5-yl --.

Column 7, line 59; after "the" insert -- European --.

Column 8, line 25; "hydrochloride, (K):" should read -- hydrochloride, m. p. (K): --.

Column 10, line 65; "33°" should read -- 233° --.

Column 10, line 65; "4-[(benzodioxan-5-" should read -- 4-(benzodioxan-5- --.

Column 10, line 66; "-1-(benzocyclohept-" should read -1-[(benzocyclohept- --.

UNITED STATES PATENT AND TRADEMARK OFFICE
CERTIFICATE OF CORRECTION

PATENT NO. : 5,194,437

DATED : Mar. 16, 1993

INVENTOR(S) : Jean-Louis Peglion, Mark Millan, Jean-Michel Rivet

It is certified that error appears in the above-indentified patent and that said Letters Patent is hereby corrected as shown below:

Column 16, line 8; delete "(R,S)-."
Column 16, approximately lines 25-32, in the formula "(V)";

reads " 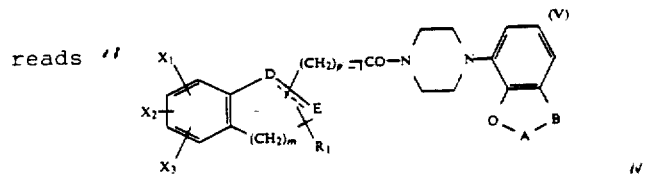

should read -- 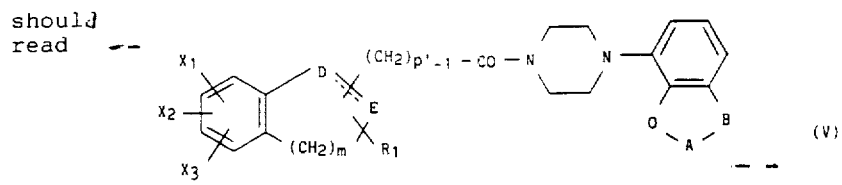

Signed and Sealed this

Twelfth Day of July, 1994

Attest:

BRUCE LEHMAN

Attesting Officer   Commissioner of Patents and Trademarks